United States Patent
Crocker et al.

(10) Patent No.: US 6,861,383 B2
(45) Date of Patent: Mar. 1, 2005

(54) CATALYST SUPPORT MATERIAL AND USE THEREOF

(75) Inventors: Mark Crocker, Amsterdam (NL); Carl Johan Gerrit Van Der Grift, Rodange (LU); Johannes Jacobus Maria Van Vlaanderen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 160 days.

(21) Appl. No.: 10/181,597

(22) PCT Filed: Jan. 19, 2001

(86) PCT No.: PCT/EP01/00739

§ 371 (c)(1),
(2), (4) Date: Jul. 18, 2002

(87) PCT Pub. No.: WO01/52982

PCT Pub. Date: Jul. 26, 2001

(65) Prior Publication Data

US 2003/0032548 A1 Feb. 13, 2003

(30) Foreign Application Priority Data

Jan. 20, 2000 (EP) ............................................ 00200230

(51) Int. Cl.[7] .......................... B01J 38/60; B01J 38/66; B01J 38/12; B01J 20/34
(52) U.S. Cl. .............................. 502/26; 502/27; 502/38
(58) Field of Search ............................... 502/26, 27, 38

(56) References Cited

U.S. PATENT DOCUMENTS

| 5,798,313 A | | 8/1998 | Carroll et al. | |
| 5,916,835 A | * | 6/1999 | Carroll et al. | ................. 502/29 |
| 5,977,009 A | * | 11/1999 | Faraj | ........................... 502/64 |

FOREIGN PATENT DOCUMENTS

| EP | 0 666 107 A2 | 8/1995 | ............ B01J/23/74 |
| WO | 98/28072 | 7/1998 | ............ B01J/21/20 |
| WO | 99/01445 | 1/1999 | ......... C07D/301/12 |
| WO | 99/49972 | 10/1999 | ............ B01J/31/40 |

* cited by examiner

*Primary Examiner*—Stanley S. Silverman
*Assistant Examiner*—Jonas N. Strickland

(57) ABSTRACT

A process for the preparation of a catalyst support material involving the steps of: (a) subjecting a used titania-on-silica catalyst to a decoking treatment, (b) washing the decoked catalyst with a washing liquid selected from an aqueous solution of a mineral acid, an aqueous solution of an ammonium salt and combinations thereof, and (c) drying and calcining the washed and decoked catalyst to yield the catalyst support material. The support material thus obtained is suitably used as support material for titania in a heterogeneous catalyst for the epoxidation of olefins into alkylene oxides.

12 Claims, No Drawings

CATALYST SUPPORT MATERIAL AND USE THEREOF

FIELD OF THE INVENTION

Background of the Invention

The present invention relates to a specific catalyst support material and to its use in a heterogeneous catalyst suitable for catalyzing the epoxidation of olefins into alkylene oxides. More specifically, the present invention relates to a process for the preparation of a catalyst support material, to a catalyst support obtainable by this process, to a process for preparing a heterogeneous epoxidation catalyst from said support material, to the epoxidation catalyst obtainable by this process and finally to the use of this epoxidation catalyst in the preparation of alkylene oxides from olefins.

It is well known in the art to produce alkylene oxides, such as propylene oxide, by epoxidation of the corresponding olefin using an active oxygen species such as hydrogen peroxide or an organic hydroperoxide as the source of oxygen. For instance, a commonly known method for manufacturing propylene oxide is the co-production of propylene oxide and styrene starting from ethylbenzene. In general such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl ethanol, and (iii) dehydrating the 1-phenyl ethanol into styrene using a suitable dehydration catalyst.

Another method for producing propylene oxide is the co-production of propylene oxide and methyl tert-butyl ether (MTBE) starting from isobutane and propene. This process is well known in the art and involves similar reaction steps as the styrene/propylene oxide production process described in the previous paragraph. In the epoxidation step tert-butyl hydroperoxide is reacted with propene forming propylene oxide and tert-butanol. Tert-butanol is subsequently etherified into MTBE.

The present invention specifically relates to the epoxidation catalyst and more in particular to suitable support materials therefor.

Titanium-containing heterogeneous epoxidation catalysts are known in the art. Examples of such catalysts are for instance described in U.S. Pat. No. 4,367,342 and EP-A-0,345,856. U.S. Pat. No. 4,367,342 discloses the use of inorganic oxygen compounds of silicon in chemical composition with at least 0.1% by weight of an oxide or hydroxide of titanium, while EP-A-0,345,856 discloses a titania-on-silica heterogeneous catalyst which is obtainable by impregnating a silicon compound with a stream of gaseous titanium tetrachloride followed by calcination and hydrolysis steps and optionally a silylation step.

When such titanium-containing heterogeneous catalysts are used to catalyse the epoxidation of propene, deactivation occurs so that at one stage they have to be replaced by fresh or regenerated catalyst. The used catalyst may either be disposed of or may be regenerated for re-use. However, one cannot limitlessly regenerate deactivated catalysts. Once a used catalyst cannot be regenerated anymore to the desired activity level it is usually disposed of. The present invention aims at providing a further application for used titania-on-silica catalysts which would normally be disposed of.

Various methods for regenerating used titania-on-silica epoxidation catalysts are known in the art. For instance, in WO 98/28072 a regeneration process for this type of catalysts is disclosed, which comprises contacting the used catalyst with a particular solvent at a temperature of from 20 to 400° C. In U.S. Pat. No. 5,798,313 a regeneration method for titanium-containing heterogeneous olefin epoxidation catalysts is disclosed, wherein the used epoxidation catalyst is heated at a temperature of at least 700° C. in the presence of oxygen. However, these methods aim at providing a re-activated catalyst by treating a deactivated catalyst in a particular way. In contrast thereto, the present invention does not aim at re-activating the used catalyst, but rather aims at converting the deactivated catalyst into a suitable support material which can be freshly loaded with catalytically active metal(s).

SUMMARY OF THE INVENTION

Accordingly, the present invention relates to a process for the preparation of a catalyst support material comprising the steps of:

(a) subjecting a used titania-on-silica catalyst to a decoking treatment,
(b) washing the decoked catalyst with a washing liquid selected from an aqueous solution of a mineral acid, an aqueous solution of an ammonium salt and combinations thereof, and
(c) drying and calcining the washed and decoked catalyst to yield the catalyst support material.

DETAILED DESCRIPTION OF THE INVENTION

As stated herein before, the used titania-on-silica catalyst treated in step (a) of the present process will normally be a catalyst which no longer has the desired activity for converting an olefin into an alkylene oxide, usually propene into propylene oxide. When the yield of propylene oxide has become undesirably low, the catalyst needs to be replaced and it is this deactivated catalyst which is useful in the present process. The used catalyst may be a catalyst which had previously been regenerated one or more times, but may also be a deactivated catalyst which deactivated for the first time and hence had not previously been subjected to a regeneration treatment.

The expression "decoking treatment" as used in the present application refers to any treatment for removing organic residues present on a catalyst by means of (substantially complete) oxidation. Accordingly, the decoking treatment of the used titania-on-silica catalyst can be attained by any method known in the art for oxidising or burning off organic material from used heterogeneous catalysts. For the purpose of the present invention it has been found particularly effective to apply a decoking treatment which comprises subjecting the used titania-on-silica catalyst to a temperature of from 300 to about 700° C., and preferably from 400 to about 550° C., in the presence of oxygen, more suitably in the presence of air, for sufficient time to burn off about 70 wt % or more, preferably about 80 wt % or more and most preferably about 90 wt % of all organic residues present on the used titania-on-silica catalyst. Preferably, the used catalyst is subjected to the decoking treatment for sufficient time to remove essentially all organic material present on the used catalyst. A typical decoking treatment, accordingly, may take from 10 minutes up to 48 hours, although a shorter period (up to 20 hours) is preferred. Most suitably the decoking treatment will take from 1 to 10 hours. The decoking typically takes place under atmospheric pressure, but in general any pressure between about 0.1 and 10 bar may be applied.

In step (b) the decoked catalyst is subjected to a washing treatment. The main aim of this washing treatment is to remove the alkali metal and alkaline earth metal ions present in and on the decoked catalyst by ion exchange, said ions having accumulated on the catalyst surface and in its pores during its use. In addition, the washing treatment is considered to re-hydroxylate the decoked catalyst's surface, which is advantageous for any metal loading step to be applied lateron. The washing treatment can take place by any washing method known the art to be capable of ensuring sufficient contact between catalyst particles and washing liquid to ensure an accurate ion exchange. Thus, suitable methods include immersing the decoked catalyst particles in the washing liquid, passing the washing liquid over a fixed bed of decoked catalyst particles or washing the decoked catalyst particles as a moving bed. The latter washing method may involve moving the catalyst particles continuously over a series of rotating trays through a washing apparatus.

It will be understood that such washing treatment may be repeated one or more times. Normally, a washing treatment will be carried out from one to ten times, suitably from one to six times. The liquid/solid ratio, i.e. volume ratio of washing liquid to solid material to be washed may vary within wide limits and suitably is from about 1 to about 15, more suitably about 2 to about 10, even more suitably from about 2.5 to about 7.5.

In an alternative embodiment of the present invention the washing may also take place continuously, suitably by passing a stream of the washing liquid continuously over a bed of decoked catalyst particles.

In accordance with the present invention it was found that a specific washing liquid should be used, namely a washing liquid selected from an aqueous solution of a mineral acid, an aqueous solution of an ammonium salt and combinations thereof. These washing liquids, namely, were found to be particularly suitable for removing the alkali metal ions and alkaline earth metal ions from the decoked catalyst, while at the same time they could re-hydroxylate the decoked catalyst's surface. Suitable mineral acids in this connection include hydrochloric acid, sulphuric acid, phosphoric acid and the like. Particularly preferred washing liquids are aqueous solutions of hydrochloric acid or sulphuric acid. Other washing liquids to be used in accordance with the present invention are aqueous solutions of an ammonium salt. Such ammonium salts' also include tetramethyl ammonium salts. Examples of suitable ammonium salts, then, include ammonium or tetramethyl ammonium hydroxide, nitrate, acetate, citrate, carbonate, chloride and sulphate. Of these, ammonium acetate is particularly preferred. Concentrations of the mineral acids or ammonium salts in water are not particularly critical and will normally range from about 0.01 M to about 5 M.

Directly after the washing step (b) and prior to drying and calcining step (c) an optional additional washing step may be applied: washing with water, preferably with distilled, demineralised or deionised water. Such an additional washing step may be useful to remove traces of the washing liquid containing alkali and/or alkaline earth metal ions from the catalyst particles. If applied, the water wash step may be repeated one or more times. Suitably, the water wash step may be carried out one to six times. The liquid/solid ratios are the same as those described above for washing step (b). Suitable ways of carrying out the water wash step are known in the art and include immersing the treated particles in water or passing water over a bed of said particles (i.e. continuous washing treatment).

Before continuing with step (c) the wash step (b) and optional subsequent water wash step may be repeated one or more times, suitably one to four times.

The drying and calcination in step (c) may also be combined in a single treatment, for instance by using a drying/calcination device containing different temperature zones. The washed decoked catalyst may then enter such device in a temperature zone having a temperature in the drying temperature range and may subsequently be passed, optionally via one or more intermediate zones operated at increasing temperatures, into a calcination zone where the temperature is in the calcination temperature range. Such combined drying/calcination treatments and devices are known in the art.

In step (c) of the process the washed particles are dried and calcined. Drying may take place in conventional ways known in the art and for the purpose of the present invention it was found particularly suitable to perform the drying in an oxygen-containing atmosphere, suitably air, at a temperature of from about 70 to about 150° C., more suitably from about 90 to about 130° C. Alternatively, the drying may take place in an atmosphere other than air, e.g. in a nitrogen atmosphere. The subsequent calcination step is suitably performed by subjecting the dried particles to a temperature which does not exceed about 500° C. and suitably is at least about 200° C. Preferred calcination temperatures are in the range of from about 230 to about 400° C., more preferably 250 to about 330° C. The calcination typically takes place in an oxygen-containing atmosphere, suitably air, but may also take place in another atmosphere, for instance in a nitrogen atmosphere. The pressure during drying and calcination is not critical and typically will be atmospheric. However, any pressure between about 0.1 and about 10 bar could be applied.

It is believed that the process as described above results in a unique carrier material which has a chemical structure different from fresh silica carrier material. Accordingly, in a further aspect the present invention relates to a catalyst support material obtainable by the process as described herein before.

More in particular, without wishing to be bound by any specific theory, it is believed that the catalyst support material obtained after step (c) of the method described above comprises silica in combination with titania, the largest part of which is present as crystalline titania at the surface of the carrier while the remainder is present as amorphous titania. More specifically, the catalyst support material in accordance with the present invention was found to comprise silica in combination with titania, of which at least about 90 wt % based on all titania present is present in the form of crystalline titania (i.e. rutile and/or anatase) with the remainder up to about 100 wt % being present as amorphous titania. More preferably, at least about 95 wt % of the titania present in the support is present in crystalline form at the surface of the support, the remainder up to about 100 wt % being present as amorphous titania. The total amount of titania (expressed in weight percent metallic titanium) present in the catalyst support material will suitably be in the range of from about 0.1 to about 7 wt %, more suitably from about 0.5 to about 5 wt % (corresponding with respectively about 0.2 to about 11.6 wt % and about 0.8 to about 8.3 wt % $TiO_2$), based on total weight of the carrier material.

The catalyst support material prepared in accordance with the present invention is very useful as support for a heterogeneous epoxidation catalyst for converting an olefin into its corresponding alkylene oxide. Accordingly, in a still further aspect the present invention relates to a process for the preparation of a heterogeneous catalyst suitable for the epoxidation of olefins into alkylene oxides, which process comprises the steps of:

(a) impregnating the catalyst support material prepared by the process as described herein before with a titanium-containing impregnating agent; and (b) calcining the impregnated support.

The impregnation step (a) is carried out using a titanium-containing impregnating agent. In step (b) the impregnated support is subsequently calcined. Calcination in step (b) is suitably performed at a temperature of at least about 300° C. and preferably does not exceed about 1000° C., while a preferred temperature range is about 400 to 900° C.

The impregnating agent used in step (a) may be either a liquid or a vapor. If a liquid impregnating agent is used, an additional drying step may be included between steps (a) and (b) to remove the solvent used in the impregnating solution. Examples of suitable liquid impregnating agents are known in the art and include solutions of titanium tetrahalide, such as titanium tetrachloride or titanium tetrafluoride, in an organic solvent, such as alkanes (e.g. hexane), aromatic compounds (e.g. toluene), alcohols (e.g. methanol, ethanol) or ethers. Other examples include organic titanium complexes such as tetra(isopropyl) titanate, tetra(n-butyl) titanate, tetrakis(trimethylsilyl) titanate and di(acetoacetyl)di(isopropyl) titanate, the latter being for instance described in JP-A-11/228553. Wet impregnation methods are also well known in the art and in principle any suitable wet impregnation technique may be used. Examples of such techniques are disclosed in GB-1,332,527; EP-A-0, 734,764 and WO-98/50374.

In a preferred embodiment, however, the catalyst support is impregnated using a gaseous titanium-containing impregnating agent. A gaseous titanium tetrahalide and in particular gaseous titanium tetra-chloride, optionally in conjunction with an inert carrier gas like nitrogen or argon, is very useful in this respect. A method using gaseous titanium tetrachloride as impregnating agent, followed by calcination, hydrolysis and optionally silylation is described in EP-A-0, 345,856. present invention. Accordingly, the present invention also relates to a process for the preparation of a heterogeneous catalyst suitable for the epoxidation of olefins into alkylene oxides, which process comprises the subsequent steps of:

(a) impregnating the catalyst support material prepared by the process as described herein before with a stream of gaseous titanium tetrahalide, suitably titanium tetrachloride, (b) calcination, (c) hydrolysis, and (d) optionally silylation.

Further details regarding steps (a) to (d) of the above catalyst preparation method can be found in EP-A-0,345,856, which is incorporated by reference herein.

The present invention also relates to heterogeneous catalysts obtainable by the catalyst preparation process as described in the previous two paragraphs. Thus, such heterogeneous catalyst composition comprises titania supported on a catalyst support material as described hereinbefore. Suitably, from about 0.5 to about 5 wt % titanium based on the weight of support material will be loaded onto the support material. Consequently, the catalyst composition may in total comprise from about 0.6 to about 12 wt % of titanium based on the total weight of the catalyst composition.

Finally, the present invention concerns a process for the preparation of an alkylene oxide by reacting an olefin with an active oxygen species in the presence of the heterogeneous catalyst composition described in the previous paragraph. Said heterogeneous catalyst is particularly useful in a process for preparing propylene oxide from propene using an active oxygen species. Suitable active oxygen species in this connection are hydrogen peroxide and organic hydroperoxides like ethylbenzene hydroperoxide and tert-butyl hydroperoxide.

The invention will be further illustrated by the following examples without limiting the scope of the invention to these particular embodiments.

EXAMPLE 1

Used titania-on-silica catalyst spheres (2 mm diameter) were subjected to a decoking treatment at 450–500° C. for approximately 5 hours. Subsequently 150 grams of the decoked catalyst spheres were washed two times with 500 ml of an aqueous 1.0 M ammonium nitrate solution (i.e. liquid/solid ratio of about 5/1) by adding the spheres to the ammonium nitrate solution and gently stirring the solution at room temperature for 90 minutes. The washed decoked catalyst spheres were then filtered and washed two times with 200 ml distilled water on a Buchner funnel. This procedure of washing with ammonium nitrate and water was repeated once. The resulting spheres were dried in air at 120° C. for two hours. Finally, the spheres were calcined in air for two hours at 300° C.

The catalyst support material thus obtained was analysed by X-ray fluorescence spectroscopy to determine the amounts of sodium, potassium and titanium. The results are indicated in Table 1.

EXAMPLE 2

Example 1 was repeated except that the washing with ammonium nitrate was replaced with a washing treatment with an aqueous sulphuric acid solution (1.0 M). This washing treatment involved two times washing with the sulphuric acid solution at a liquid/solid ratio of 2.5.

The results are indicated in Table 1.

Furthermore, the catalyst support material obtained was analysed by X-ray diffraction spectroscopy to determine the amounts of crystalline and amorphous titania. It was found that of all titania present (i.e. 2.6 wt % as metallic Ti or 4.3 wt % as $TiO_2$), 98 wt % was present as crystalline titania (35.6 wt % anatase and 62.4 wt % rutile) and only 2 wt % was present as amorphous titania.

COMPARATIVE EXAMPLE 1

Example 1 was repeated except that no washing treatment at all was performed after the decoking treatment. The results are indicated in Table 1.

Furthermore, the catalyst support material obtained was analysed by X-ray diffraction spectroscopy to determine the amounts of crystalline and amorphous titania. It was found that of all titania present (i.e. 2.9 wt % as metallic Ti or 4.8 wt % as $TiO_2$), 88 wt % was present as crystalline titania (25 wt % anatase and 63 wt % rutile) and 12 wt % was present as amorphous titania.

COMPARATIVE EXAMPLE 2

Example 1 was repeated except that the washing treatment with ammonium nitrate was dispensed with and a demi-water washing was performed: five times at liquid/solid ratio of 3.5. The results are indicated in Table 1.

EXAMPLE 3

The carrier prepared in Example 1 was impregnated with a stream of gaseous titanium tetrachloride in accordance with the method disclosed in EP-A-0,345,856, i.e. by the subsequent steps of impregnation, calcination, hydrolysis and silylation. An additional 2.23 wt % titanium was loaded onto the catalyst support, so that the total titanium content amounted 5.16 wt %.

This catalyst was used in an epoxidation experiment carried out in a continuous epoxidation bench scale unit containing two vessels on automatic weight balances containing respectively the EBHP and propene feed streams, two high pressure pumps, a fixed bed reactor, a third pump for pumping a recycle stream over the reactor, means to maintain the reactor continuously at temperatures between 60 and 120° C., a stripper to remove light boiling components like propene, a cooler and a vessel for receiving the product.

The propene feed and the EBHP feed (a 35 wt % solution of EBHP in ethylbenzene) were supplied to the reactor via the two high pressure pumps and mixed together before entering the reactor. The reactor was operated liquid full at 48 bara pressure and 90° C. The catalyst bed in the reactor consisted of 5.0 grams of the catalyst prepared. A large recycle stream was maintained over the reactor to have isothermal operation of the reactor bed. The mixed feed of propene and 35 wt % EBHP solution in ethylbenzene was mixed with the recycle stream prior to introduction into the reactor.

A compositional analysis of the reaction mixture was carried out by means of Super Critical Fluid Chromatography (SFC).

The following process conditions were maintained:

| | |
|---|---|
| throughput EBHP in EB | 15.25 grams/hour |
| throughput propene | 9.75 grams/hour |
| propene/EBHP molar ratio | 6 |
| recycle flow | 5 kg/hour. |

From the SFC data the EBHP conversion and the propylene oxide selectivity were determined, the results are indicated in Table 1.

EXAMPLE 4

Example 3 was repeated, but with the catalyst support material of Example 2 in stead of the support material of Example 1. The results are indicated in Table 1.

COMPARATIVE EXAMPLE 3

Example 3 was repeated, but with the catalyst support material of Comparative Example 1 in stead of the support material of Example 1. The results are indicated in Table 1.

COMPARATIVE EXAMPLE 4

Example 3 was repeated, but with a fresh silica support material in stead of the support material of Example 1. The results are indicated in Table 1.

Furthermore, the catalyst used in this Comparative Example was analysed by X-ray diffraction spectroscopy to determine the amounts of crystalline and amorphous titania. It was found that of all titania present (i.e. 4.4 wt % as metallic Ti or 7.3 wt % as $TiO_2$), 34 wt % was present as crystalline titania (12 wt % anatase and 22 wt % rutile) and 66 wt % was present as amorphous titania.

TABLE 1

| | Results | | | | |
|---|---|---|---|---|---|
| | Ti (wt %) | Na (wt %) | K (wt %) | EBHP conversion (%) | PO selectivity (%) |
| Example 1 | 2.9 | 0.1 | n.d. | — | — |
| Example 2 | 2.6 | 0.1 | n.d. | — | — |
| Comp Example 1 | 2.9 | 0.4 | 0.02 | — | — |
| Comp Example 2 | 2.9 | 0.4 | n.d. | — | — |
| Example 3 | 5.2 | 0.1 | n.d. | 89.4 | 93.9 |
| Example 4 | 4.4 | 0.1 | n.d. | 89.2 | 92.6 |
| Comp Example 3 | 4.4 | 0.4 | n.d. | 85.7 | 94.5 |
| Comp Example 4 | 4.4 | n.d. | n.d. | 90.4 | 88.6 |

Notes:
1. n.d. means not detectable; detection limit for K is 0.01 +/− 0.02 wt %, for Na it is 0.07 wt % +/− 0.05 wt %;
2. Ti, Na and K in weight percent (wt %) refer to the amounts of respectively titanium, sodium and potassium in the catalyst support material (Examples 1 and 2 and Comparative Examples 1 and 2) or in the actual catalyst (Examples 3 and 4 and Comparative Examples 3 and 4).

From Table 1 it can be seen that the support materials prepared in accordance with the present invention (Examples 1 and 2) contain significantly less sodium than support materials prepared in other ways (Comparative Examples 1 and 2). Furthermore, the epoxidation catalysts based on the carrier materials of the invention (Examples 3 and 4) exhibit a better activity/selectivity combination than both catalyst based on unwashed support material (Comparative Example 3) and fresh silica as support material (Comparative Example 4).

Furthermore, it can be seen from the X-ray diffraction data of Example 2 and Comparative Examples 1 and 4 that a titania-silica catalyst support material, wherein at least 90 wt % of all titania present is present in the form of crystalline titania, was not available before.

We claim:

1. A process comprising the steps of:
   (a) subjecting a used titania-on-silica catalyst to a decoking treatment;
   (b) washing the decoked catalyst with a washing liquid selected from the group consisting of an aqueous solution of a mineral acid, an aqueous solution of an ammonium salt and combinations thereof; and
   (c) drying and calcining the washed and decoked catalyst to yield a catalyst support material.

2. The process of claim 1, wherein the decoking treatment comprises subjecting the used titania-on-silica catalyst to a temperature of from about 300 to about 700° C. in the presence of oxygen.

3. The process of claim 1, wherein in step (b) an aqueous solution of hydrochloric acid or sulphuric acid is used.

4. The process of claim 1, wherein in step (b) an aqueous solution of an ammonium salt is used.

5. The process of claim 4, wherein the ammonium salt is ammonium acetate.

6. The process of claim 1, wherein after step (b) and prior to step (c) an additional washing step with water is carried out.

7. The process of claim 1, wherein the calcination temperature in step (c) does not exceed about 500° C.

8. The process of claim 1, which process comprises the subsequent steps of:
  (d) impregnating the catalyst support material obtained in step (c) with a titanium-containing impregnating agent; and,
  (e) calcining the impregnating support.

9. The process of claim 8, wherein the titanium-containing impregnating agent is a liquid impregnating agent.

10. The process of claim 8, wherein the titanium-containing impregnating agent is a gaseous impregnating agent.

11. The process of claim 10, which process comprises the subsequent steps of:
  (d) impregnating the catalyst support material obtained in step (c) with a gaseous titanium tetrahalide;
  (e) calcining the impregnated support material;
  (f) hydrolyzing the calcined material obtained from step (e); and,
  (g) optionally silylating the product from step (f).

12. The process of claim 11, wherein the gaseous titanium tetrahalide used in step (d) is a gaseous titanium tetrachloride.

* * * * *